United States Patent [19]

Braish et al.

[11] Patent Number: 5,196,548

[45] Date of Patent: Mar. 23, 1993

[54] PREPARATION OF DIAZABICYCLIC INTERMEDIATES

[75] Inventors: Tamim F. Braish, Ledyard; Darrell E. Fox, Pawcatuck, both of Conn.

[73] Assignee: Pfizer Inc., New York, N.Y.

[21] Appl. No.: 908,840

[22] Filed: Jul. 2, 1992

Related U.S. Application Data

[60] Continuation of Ser. No. 665,380, Mar. 4, 1991, abandoned, which is a division of Ser. No. 423,063, Oct. 18, 1989, Pat. No. 5,036,153, which is a continuation-in-part of Ser. No. 350,423, May 11, 1989, abandoned.

[51] Int. Cl.$^5$ .............................................. C07D 209/02
[52] U.S. Cl. ...................... 548/453; 548/452; 548/532; 548/542
[58] Field of Search ................ 548/453, 532, 542

[56] References Cited

U.S. PATENT DOCUMENTS

| | | | |
|---|---|---|---|
| 2,932,650 | 4/1960 | Cope et al. | 548/453 |
| 3,910,950 | 10/1975 | Miller | 548/453 |
| 3,947,445 | 9/1976 | Henry | 260/268 BF |
| 5,036,153 | 7/1991 | Braish et al. | 548/453 |

FOREIGN PATENT DOCUMENTS

| | | |
|---|---|---|
| 0324543 | 7/1989 | European Pat. Off. |
| 1470060 | 7/1969 | Fed. Rep. of Germany |

OTHER PUBLICATIONS

The Journal of Organic Chemistry, vol. 31, 1966 P. S. Portoghese et al., pp. 1059–1062.
Baker et al J. OCS, 46, (1981), pp. 2954–2960.

*Primary Examiner*—David B. Springer
*Attorney, Agent, or Firm*—Peter C. Richardson; Paul H. Ginsburg; Valerie Fedowich

[57] ABSTRACT

Diazabicyclo[2.2.1]heptane intermediates are prepared from 4-hydroxy-L-proline in a five step procedure, or from allo-4-hydroxy-D-proline, through a novel 2-($C_1$–$C_6$)alkyl-5-substituted-2,5-diazabicyclo[2.2.1]heptane intermediate. The diazabicycloheptanes are of use in the preparation of antibiotic quinolones.

12 Claims, No Drawings

PREPARATION OF DIAZABICYCLIC INTERMEDIATES

This is a continuation of application Ser. No. 07/665,380, filed on Mar. 4, 1991, abandoned, which is a division of U.S. Ser. No. 07/423,063, filed Oct. 18, 1989, now U.S. Pat. No. 5,036,153, which is a continuation-in-part of U.S. Ser. No. 350,423, filed May 11, 1989, now abandoned.

BACKGROUND OF THE INVENTION

The invention relates to the preparation of 2,5-diazabicyclo[2.2.1]heptane intermediates of use in the preparation of antibiotic quinolones such as disclosed in U.S. Pat. No. 4,775,668.

A method for the synthesis of 2,5-diazabicyclo[2.2.1]heptanes is described in Portoghese et al, J. Org. Chem., 31, 1059 (1966). According to this method, hydroxy-L-proline is transformed into tritosylhydroxy-L-prolinol which is first reacted with benzylamine and then hydrogen iodide, phosphorus, and acetic acid to form 2-benzyl-2,5-diazabicyclo[2.2.1]heptane dihydroiodide. U.S. Pat. No. 3,947,445 follows a similar procedure and then converts the dihydroiodide through a three step procedure into 2-methyl-2,5-diazabicyclo[2.2.1]heptane.

SUMMARY OF THE INVENTION

The invention relates to a process for preparing a 2,5-diazabicyclo[2.2.1]heptane derivative of the formula IA

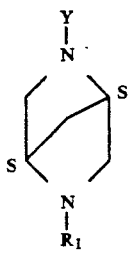

or the enantiomer, racemate, or acid addition salt thereof, wherein Y is hydrogen or $XR_2$, $R_1$ is hydrogen or $C_1$–$C_6$ alkyl, and X and $R_2$ are as defined below, by (a) reacting a compound of the formula

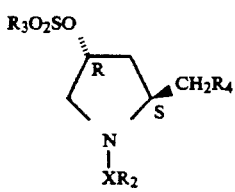

or the enantiomer or the racemate thereof, wherein X is $SO_2$ or $CO_2$, $R_2$ and $R_3$ are each independently $C_1$–$C_6$ alkyl, trifluoromethyl, benzyl, or phenyl optionally substituted by one or two $C_1$–$C_6$ alkyl, halogen, nitro, methoxy or trifluoromethyl, and $R_4$ is halogen or $OSO_2R_3$ wherein $R_3$ is as defined above, with a ($C_1$–$C_6$) alkylamine or ammonia to form a compound of the formula IA wherein Y is $XR_2$, and X, $R_1$ and $R_2$ are as defined above, and, if desired, (b) reducing or hydrolyzing the compound of formula IA wherein Y is $XR_2$ to form a compound of formula IA wherein Y is hydrogen.

In a preferred embodiment of this process, said $C_1$–$C_6$ alkylamine is methylamine, X is $SO_2$, and $R_2$ is p-tolyl.

The invention also relates to a compound of the formula II

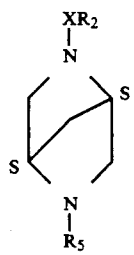

or the enantiomer or racemate thereof, wherein X is $SO_2$ or $CO_2$, $R_2$ is $C_1$–$C_6$ alkyl, trifluoromethyl, benzyl, or phenyl optionally substituted by one or two $C_1$–$C_6$ alkyl, halogen, nitro, methoxy or trifluoromethyl, and $R_5$ is $C_1$–$C_6$ alkyl.

Preferably, X is $SO_2$, and $R_2$ is paratolyl in formula II, and more preferably, $R_5$ is methyl, X is $SO_2$, and $R_2$ is paratolyl. The compounds of formula II have optical centers and therefore occur in two different stereoisomeric configurations, the S,S-configuration and the R,R-configuration. The present invention includes both stereoisomers of the compounds of formula II, and also the racemic mixture thereof. The formulas herein indicate the particular R or S configuration with the designation "R" and "S", respectively.

The invention further relates to a process for preparing a compound of above formula III, wherein X is $SO_2$ or $CO_2$ and $R_2$ is as defined above, by reacting a compound of the formula

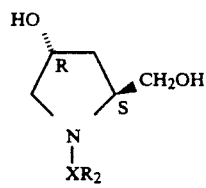

or the enantiomer or racemate thereof, wherein X is $SO_2$ or $CO_2$, with a compound of the formula $R_3SO_2X^1$     V wherein $R_3$ is $C_1$–$C_6$ alkyl, trifluoromethyl, or phenyl optionally substituted by one or two $C_1$–$C_6$ alkyl, halogen, nitro, methoxy or trifluoromethyl, and $X^1$ is halogen or $OSO_2R_3$ wherein $R_3$ is as defined above. In a preferred embodiment, $R_2$ is paratolyl and X is $SO_2$ in formula IV.

The invention also relates to a process for preparing a compound of above formula IV by reducing a compound of the formula

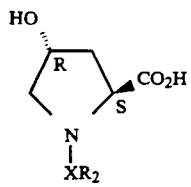

or the enantiomer or racemate thereof, wherein X is $SO_2$ or $CO_2$, and $R_2$ is $C_1$-$C_6$ alkyl, trifluoromethyl, or phenyl optionally substituted by one or two $C_1$-$C_6$ alkyl, halogen, nitro, methoxy or trifluoromethyl. In a preferred embodiment, the reduction is carried out with sodium borohydride in the presence of borontrifluoride etherate. In another preferred embodiment, X is $SO_2$ and $R_2$ is paratolyl in formula VI.

The invention further relates to a process for preparing a compound of formula VI by reacting 4-hydroxy-L-proline with a compound of the formula

wherein X is $SO_2$ or $CO_2$, $R_2$ is $C_1$-$C_6$ alkyl, trifluoromethyl, benzyl, or phenyl optionally substituted by one or two $C_1$-$C_6$ alkyl, halogen, nitro, methoxy or trifluoromethyl, and $X^1$ is halogen, an azide or $OSO_2R_2$, wherein $R_2$ is as defined above, in the presence of alkali metal carbonate. In a preferred embodiment, X is $SO_2$ and $R_2$ is paratolyl in formula VII.

The invention further relates to an alternative process for preparing the R,R-stereoisomers of the formula IA

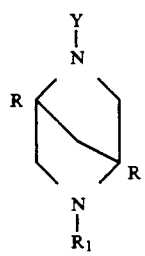

or an acid addition salt thereof, wherein $R_1$ is hydrogen or $C_1$-$C_6$ alkyl, Y is hydrogen or $XR_2$, X is $SO_2$ or $CO_2$, and $R_2$ is $C_1$-$C_6$ alkyl, trifluoromethyl, benzyl, or phenyl optionally substituted by one or two $C_1$-$C_6$ alkyl, halogen, nitro, methoxy, or trifluoromethyl, by (a) reacting a compound of the formula

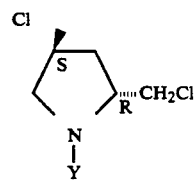

wherein Y is as defined above, with a $C_1$-$C_6$ alkylamine or ammonia to form a compound of the formula IA wherein Y is $XR_2$, and X, $R_1$ and $R_2$ are as defined above, and, if desired, (b) reducing or hydrolyzing a compound of formula IA wherein Y is $XR_2$ to form a compound of formula IA wherein Y is hydrogen. In a preferred embodiment, the $C_1$-$C_6$ alkylamine is methylamine and Y is paratolylsulfonyl in step (a).

The invention also relates to a compound of the formula

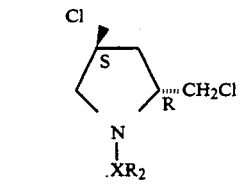

wherein X is $SO_2$ or $CO_2$ and $R_2$ is $C_1$-$C_6$ alkyl, trifluoromethyl, benzyl, or phenyl optionally substituted by one or two $C_1$-$C_6$ alkyl, halogen, nitro, methoxy, or trifluoromethyl. In a preferred embodiment, X is $SO_2$ and $R_2$ is p-tolyl.

The invention further relates to a process for preparing a compound of the formula

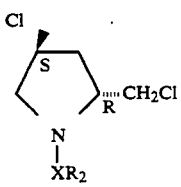

wherein X is $SO_2$ or $CO_2$, and $R_2$ is $C_1$-$C_6$ alkyl, trifluoromethyl, benzyl, or phenyl optionally substituted by one or two $C_1$-$C_6$ alkyl, halogen, nitro, methoxy, or trifluoromethyl, by heating a compound of the formula

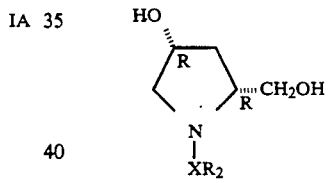

with tosylchloride in pyridine.

DETAILED DESCRIPTION OF THE INVENTION

The term "alkyl" in the definitions of groups $R_1$, $R_2$, $R_3$, $R_4$ and $R_5$ denotes saturated monovalent straight or branched aliphatic hydrocarbon radicals such as methyl, ethyl, propyl, t-butyl, hexyl, etc. The term "halogen" denotes fluoro, chloro, bromo, or iodo.

Scheme A set out below shows the reaction scheme for the preparation of the S,S-stereoisomer of the compound of formula I from trans-4-hydroxy-L-proline, including the process steps according to the invention set out above. The correct stereoisomeric configuration is shown in each one of the formulae by designation of "R" and "S" at the optical centers in each formula. The R,R-stereoisomer of the compound of formula I may be prepared in a similar manner from the enantiomer of the compound of formula IV which may be prepared starting from allo-4-hydroxy-D-proline, described in Baker et al, J. Org. Chem., Vol. 46, 2955 (1981).

The formulae given in this Scheme and throughout the present application conform to the accepted convention for indicating stereoisomers, namely, " ||||||||| " to indicate an atom projecting into the plane of the paper (α-orientation) and "◄" to indicate an atom projecting out from the plane of the paper (β-orientation) and hence the plane of the molecule itself.

The above process for preparing a compound of formula I (the compounds of formula IA wherein Y is hydrogen) by reduction or hydrolysis of a compound of formula II (the compounds of formula IA wherein Y is XR$_2$) is conveniently carried out by reaction of compound (II) with an aqueous or anhydrous hydrogen halide such as hydrogen chloride, hydrogen iodide and hydrogen bromide, in an acid solvent, such as acetic acid or sulfuric acid.

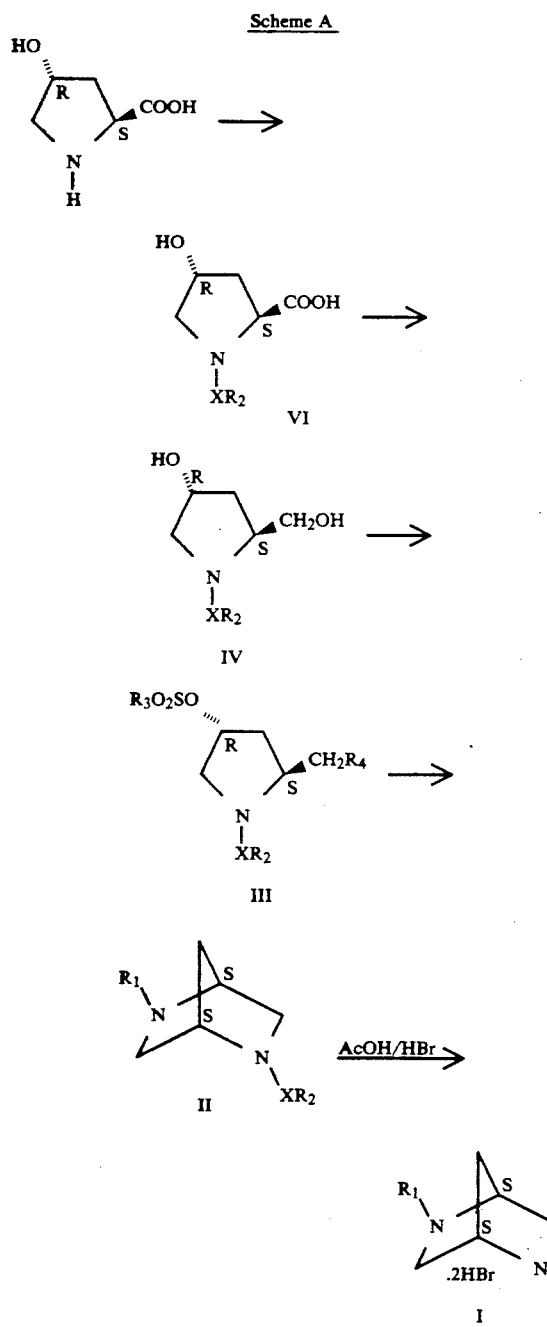

the reaction with hydrogen chloride is a hydrolysis, and the reaction with hydrogen bromide or hydrogen iodide is a reduction, as disclosed in Searles et al, Chem. Review, 1077-1103 (1959). The acid solvent used may be an organic acid such as acetic acid or an inorganic acid such as sulfuric acid. Preferably, the reaction is carried out with aqueous or anhydrous hydrogen bromide in acetic acid. The reaction is generally carried out at temperatures of from about room temperature to about 100° C., preferably at room temperature.

Alternatively, compound (I) may be formed from compound (II) by the electrochemical reductive cleavage in a mixture of water and an organic solvent in the presence of an organic electrolyte. Examples of suitable organic solvents are acetonitrile and acetic acid. An example of a suitable organic electrolyte is a tetra(C$_1$–C$_6$)alkylammonium halide such as tetraethylammonium bromide. The reaction temperature is usually from room temperature to about 50° C.

The above process for producing compound (II) from compound (III) is generally conducted with excess alkylamine, preferably at least about three molar equivalents alkylamine. The reaction is usually carried out in a sealed container depending on the alkylamine used. For instance, methylamine and ethylamine are gases at the reaction temperatures and thus require reaction in a sealed container. Generally, the reaction is conducted in an alcoholic solvent or water, preferably methanol or water. The reaction temperature ranges from about 50° to about 130° C., and is generally about 90° C.

The process for preparing compound (III) from compound (IV) is conveniently conducted in an inert solvent. Suitable solvents are non-polar solvents such as toluene and benzene. The reaction is conducted in the presence of a base. Suitable bases are aliphatic organic bases such as tertiary-(C$_1$–C$_6$)alkyl amine, e.g. triethylamine, or an aromatic organic base such as 2,6-lutidine, pyridine, (C$_1$–C$_6$)alkyl-substituted pyridine or N,N-dimethyl-4-aminopyridine. Preferably, the reaction is conducted in pyridine which acts both as a base and a solvent. The compound (V) is present in excess of two molar equivalents, preferably in an amount of about three molar equivalents. The reaction temperature is about 0° to about 50° C., usually about 15° C. (IV) is carried out with a hydride of a metal in Group III of the Periodic Table, such as lithium aluminum hydride or diborane. The reduction is carried out in the presence of an ether solvent. Suitable solvents are di(C$_1$–C$_6$)alkyl ethers, glyme, diglyme and, preferably, tetrahydrofuran. The diborane is preferably generated in situ from the reaction of sodium borohydride with borontrifluoride etherate. The reduction is conducted at temperatures ranging from about 0° to about 45° C., usually about room temperature.

The reaction to form compound (VI) from 4-hydroxy-L-proline and R$_2$XX$^1$ is generally conducted in a polar solvent such as water. The reaction is in the presence of an alkali metal carbonate, preferably sodium carbonate. The reaction temperature ranges from about 10° to about 50° C., usually about room temperature.

The R,R-stereoisomers of formula II may be prepared from allo-4-hydroxy-D-proline as set out in Scheme B. The last step in Scheme B is identical to the last step in Scheme A except for the stereochemistry of the compounds of formulae I and II.

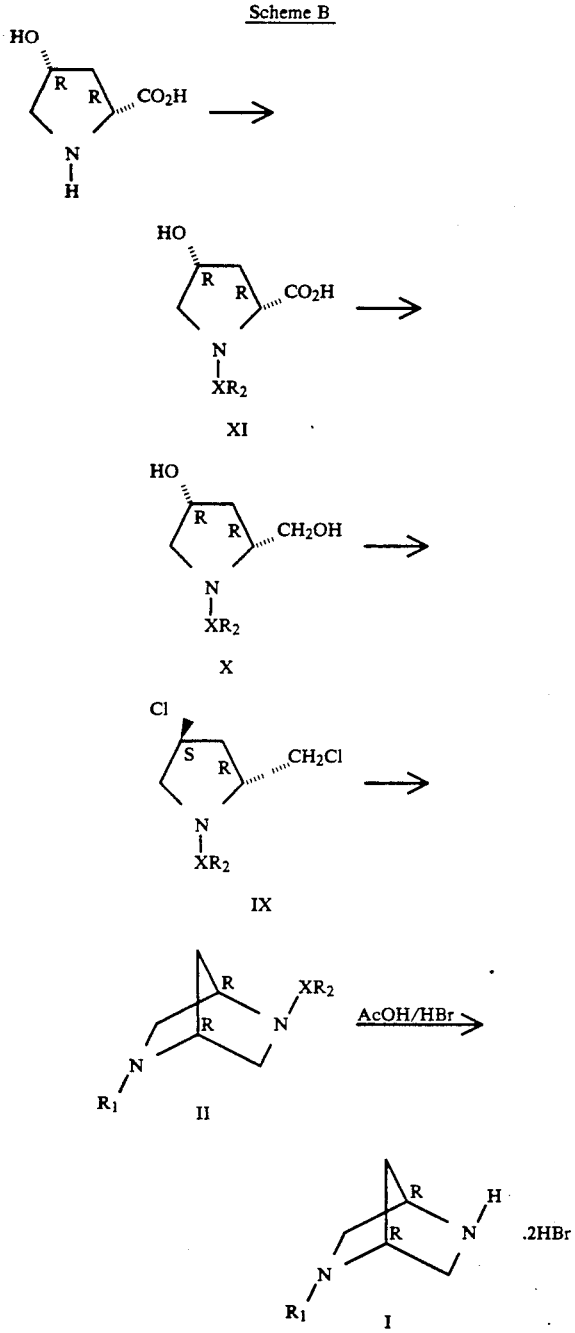

Scheme B

The compounds of formula II in Scheme B are prepared by reacting the compounds of formula IX with a $C_1$–$C_6$ alkylamine or ammonia. The process is generally conducted with excess alkylamine, preferably at least about three molar equivalents alkylamine. The reaction is usually carried out in a sealed container depending on the alkylamine used. For instance, methylamine and ethylamine are gases at the reaction temperatures and thus require reaction in a sealed container. Generally, the reaction is conducted in an alcoholic solvent or water, preferably methanol or water. The reaction temperature ranges from about 50° to about 130° C., and is generally about 90° C.

The compounds of formula IX are prepared by reacting compounds of the formula X with tosylchloride in pyridine. The reaction is conducted at temperatures of about 70° to about 115° C., generally at about 90° C. Under these reaction conditions, the R,R-stereoisomers of the formula X converts to the R,S-stereoisomer of the compounds of formula IX.

The R,R-stereoisomers of formula X are prepared in identical manner as the R,S-compounds of formula IV in Scheme A by reduction of the R,R-compounds of formula XI with a hydride in the presence of an ether solvent, as outlined above.

The R,R-compounds of formula XI are prepared in identical manner as the R,S-stereoisomers of formula VI in Scheme A by reaction of allo-4-hydroxy-D-proline with $R_2XX^1$ in a polar solvent such as water in the presence of an alkali metal carbonate, preferably sodium carbonate, at a reaction temperature ranging from about 10° to about 50° C., usually about room temperature.

The following Examples illustrate the invention.

EXAMPLE 1

1-(4-Toluenesulfonyl)-4-hydroxy-L-proline

To a solution of 100 g (763 mmol) of 4-hydroxy-L-proline in 750 ml of water was added 169.9 g (1602 mmol) of sodium carbonate at 0° C. along with 174.5 g (916 mmol) of 4-toluenesulfonyl chloride (added in 3 portions over a period of 1 hour). The slurry was then warmed to room temperature and allowed to stir for 48 hours. The reaction was acidified with concentrated hydrogen chloride solution to pH 2 and the product was isolated via filtration. The filter cake was washed with pH 2 buffer and dried in a vacuum oven at 60° C. for 16 hours to obtain 215.3 g of the product as a white crystalline solid in 99% yield. M.P.=149°–151° C.

EXAMPLE 2

(2S, 4R)-2-Hydroxymethyl-4-hydroxy-1-(4-toluenesulfonyl)-pyrrolidine

To 2 l of tetrahydrofuran (THF) was added 57.6 g (1523 mmol) of sodium borohydride and the mixture was cooled to 10° C. before 250 ml (1980 mmol) of borontrifluoride etherate was added dropwise over a period of 1 hour. Then 215.3 g (755.4 mmol) of 1-(4-toluenesulfonyl)-4-hydroxy-L-proline was added carefully in 100 ml of THF and the mixture was allowed to stir for 16 hours. The reaction was quenched with methanol and 10% aqueous hydrogen chloride solution was added and the mixture was gently heated to 60° C. for 1 hour. The reaction mixture was filtered and the pH was adjusted to neutral with 50% aqueous sodium hydroxide solution and the volatiles were evaporated under reduced pressure. The product was then isolated via filtration and the filter cake was washed with water. Drying under vacuum at 60° C. for 12 hours yielded 164 g of the product as a white solid in 85% yield. M.P. 132°–133° C.

EXAMPLE 3

(2S, 4R)-1-(4-Toluenesulfonyl)-2-(4-toluenesulfonyloxymethyl)-4-(4-toluenesulfonyloxy)-pyrrolidine To an ice-cold solution of 170 g (626.5 mmol) of (2R, 4S)-2-hydroxymethyl-4-hydroxy-1-p-toluenesulfonyl)-pyrrolidine in 0.5 l of pyridine was added 250 g (1.32 mol) of p-toluenesulfonyl chloride in 1 portions in order to keep the temperature of the reaction below 15° C. for 1 hour and then warmed to room temperature. After 12 hours an additional 125 g (656 mmol) of p-toluenesulfonyl chloride was added and the mixture was allowed to stir at room temperature for 16 additional hours. The mixture was then cooled with an ice bath and 3 l of 10% aqueous hydrogen chloride solution was carefully added. A white precipitate formed which was isolated via filtration and then taken in 1 l of ethanol and heated to reflux for 30 minutes. The mixture was then cooled and the solids were filtered and dried under reduced pressure to give 213 g of product in 80% yield. M.P.=134°-135° C.

EXAMPLE 4

(2S, 4R)-1-(4-Toluenesulfonyl)-2-(chloromethyl)-4-(4-toluenesulfonyloxy)-pyrrolidine To an ice-cold solution of 170 g (626.5 mmol) of (2R, 4S)-2-hydroxymethyl-4-hydroxy-1-(4-toluenesulfonyl)-pyrrolidine in 0.5 l of pyridine was added 250 g (1.32 mol) of p-toluenesulfonyl chloride in one portion and the reaction was warmed to 50° C. After 6 hours the mixture was cooled with an ice bath and 3 l of 10% aqueous hydrogen chloride solution was carefully added. A white precipitate formed which was isolated via filtration and then taken in 1 l of ethanol and heated to reflux for 30 minutes. The mixture was then cooled and the solids were filtered and dried under reduced pressure to give 195 g of product in 70% yield. M.P.=145°-146° C.

EXAMPLE 5

(1S, 4S)-2-(4-Toluenesulfonyl)-5-methyl-2,5-diazabicyclo-[2.2.1]heptane

A Parr bottle was charged with 115 g (198.4 mmol) of (2S, 4R)-1-(4-toluenesulfonyl)-2-(p-toluenesulfonyloxymethyl)-4-(4-toluenesulfonyloxy)-pyrrolidine and 690 ml of methanol and the bottle was then tared. Methylamine gas was bubbled through the methanol solution until 62 g (2 mol) of the gas has dissolved. The bottle was then sealed and heated to 90° C. After heating for 16 hours the reaction was cooled and the solvent was evaporated at reduced pressure. The residual solids were then partitioned between 500 ml of methylene chloride and 400 ml of 10% aqueous sodium hydroxide solution. The layers were separated and the organic layer was washed with 400 additional ml of 10% aqueous sodium hydroxide solution, and then dried over sodium sulfate. Evaporation of the solvent under reduced pressure provided 47.5 g of the desired product which represents a 90% yield. M.P.=87°-88° C.

EXAMPLE 6

(1S, 4S)-2-(4-Toluenesulfonyl)-5-methyl-2,5-diazabicyclo-[2.2.1]heptane

A Parr bottle was charged with 3.8 g (8.56 mmol) of (2S, 4R)-1-(4-toluenesulfonyl)-2-(chloromethyl)-4-(4-toluenesulfonyloxy)-pyrrolidine and 25 ml of methanol and the bottle was then tared. Methylamine gas was bubbled through the methanol solution until 2.65 g (85.6 mmol) of the gas had dissolved. The bottle was then sealed and heated to 90° C. After heating for 16 hours the reaction was cooled and the solvent was evaporated at reduced pressure. The residual solids were then partitioned between 50 ml of methylene chloride and 40 ml of 10% aqueous sodium hydroxide solution. The layers were separated and the organic layer was washed with 30 additional ml of 10% aqueous sodium hydroxide solution, and then dried over sodium sulfate. Evaporation of the solvent under reduced pressure provided 1.73 g of the desired product which represents a 76% yield. M.P.=87°-88° C.

EXAMPLE 7

(1S, 4S)-2-Methyl-2,5-diazabicyclo-[2.2.1]-heptane, dihydrobromide 60 g (225 mmol) of (1S, 4S)-2-(4-Toluenesulfonyl)-5-methyl-2,5-diazabicyclo-[2.2.1]heptane was suspended in 900 ml of 30% hydrogen bromide in acetic acid and the mixture was allowed to stir at room temperature. After 6 hours the acetic acid was removed under aspirator pressure to ¼ of the original volume and 1800 ml of ethylacetate was then added. A solid precipitated and was filtered under an inert atmosphere. The product was recrystallized by dissolving in a minimum amount of methanol at reflux. Cooling followed by the addition of 400 ml of isopropyl alcohol provided a white solid which was filtered and dried under reduced pressure. The product weighed 48 g which represents an 81% yield. M.P.=258°-259° C. (coloration occurs at 234° C.). $[\alpha]_D = +13.21°$ (c=0.946, CH$_3$OH)

EXAMPLE 8

Allo-4-cis-hydroxy-D-proline ethyl ester hydrochloride 80 g of 4-cis-hydroxy-D-proline (0.61 mol) was suspended in 500 ml of anhydrous ethanol and anhydrous HCl gas was allowed to bubble through the mixture until the reaction became homogeneous. The reaction was then heated to reflux for 5 hours and the volume of the solvent was reduced by one half. 100 ml of diethylether was added and the mixture was kept in a freezer overnight. The resulting precipitate was filtered and washed with diethylether and dried under reduced pressure to yield 111 g of product (93% yield). M.P. 152°-153° C.

EXAMPLE 9

Allo-1-(4-Toluenesulfonyl)-4-(4-toluenesulfonyloxy)-D-proline ethyl ester

To 110 g (562 mmol) of the allo-4-hydroxy-D-proline ethyl ester hydrochloride was added 1 liter of pyridine and 79 ml of triethylamine at 0° C. After stirring the mixture for 10 minutes, 242.1 g (1.24 mol) of p-toluenesulfonyl chloride was added in small portions to control the temperature between 0°-5° C. and the reaction was allowed to stir at 0° C. overnight. The next day the reaction was added to 750 ml of ice cold water and the slurry was left to stir at room temperature for 1 hour. The solids were filtered and dried in a vacuum oven at 30° C. for 48 hours to provide 243.9 g of product (92% yield). M.P.=122°-123° C.

EXAMPLE 10

4-(Acetyloxy)-1-(4-toluenesulfonyl)-D-proline ethyl ester

To 218 g (466 mmol) of allo-1-(4-toluenesulfonyl)-4-(4-toluenesulfonyloxy)-D-proline ethyl ester in 1500 ml of toluene was added 81 g (606 mmol) of tetramethyl ammonium acetate and the mixture was heated to reflux for 2 hours. The reaction was cooled, washed with 2×500 ml of water and dried over sodium sulfate. Evaporation of the solvent and drying the resulting solids in a vacuum oven overnight at 30° C. provided 120.6 g of product (72% yield). M.P.=82°-83° C.

EXAMPLE 11

1-(4-Toluenesulfonyl-4-hydroxy-D-proline

To 127.9 g (359.9 mmol) of 4-(acetyloxy)-1-(4-toluenesulfonyl)-D-proline ethyl ester in 640 ml of THF was added 100 g (1.8 mol) of KOH dissolved in 640 ml of water at 0° C. The mixture was warmed to room temperature and allowed to stir for 2 hours. The organic solvents were removed in vacuo and the Ph of the resulting mixture was adjusted to neutral with concentrated HCl. A precipitate formed which was filtered and dried overnight in a vacuum oven at 25° C. to provide 86.2 g of product (84% yield). M.P.=147°-149° C.

EXAMPLE 12

(2R, 4S)-2-Hydroxymethyl-4-hydroxy-1-(4-toluene-sulfonyl)-pyrrolidine

To 900 ml of THF was added 21.75 g (574.9 mmol) of sodium borohydride and the mixture was cooled to 10° C. before 97.92 ml (776.2 mmol) of borontrifluoride etherate was added dropwise over a period of 1 hour. Then 82 g (287.4 mmol) of N-(4-toluenesulfonyl)-4-hydroxy-D-proline was added carefully in 300 ml of THF at 0° C. and the mixture was warmed to room temperature and allowed to stir for 16 hours. The reaction was cooled to 0° C. and quenched with methanol; 10% aqueous HCl solution was then added and the mixture was gently heated to 60° C. for 1 hour. The pH of the reaction was adjusted to neutral with 50% aqueous sodium hydroxide solution and the volatiles were evaporated under reduced pressure. The product was then isolated via filtration and the filter cake was washed with water. Drying under vacuum at 60° C. for 12 hours yielded 78 g of the product as a white solid in 100% yield. M.P.=131°-132° C.

EXAMPLE 13

(2R, 4S)-1-(4-Toluenesulfonyl)-2-(4-toluenesulfonyloxymethyl)-4-(4-toluenesulfonyloxy)-pyrrolidine This compound was prepared from the compound of Example 12 by the process described in Example 3. M.P.×125°-130° C.

EXAMPLE 14

(2R, 4S)-1-(4-Toluenesulfonyl)-2-chloromethyl-4-(4-toluenesulfonyloxy)-pyrroline This compound was prepared from the compound of Example 13 by the process described in Example 4. M.P.×141°-143° C.

EXAMPLE 15

(1R, 4R)-2-(4-Toluenesulfonyl)-5-methyl-2,5-diazabicyclo-[2.2.1]heptane

This compound was prepared from the compound of Example 14 by the process described in Examples 5 and 6. M.P.×82°-87° C.

EXAMPLE 16

(1R, 4R)-2-Methyl-2,5-diazabicyclo-[2.2.1]-heptane, dihydrobromide

This compound was prepared from the compound of Example 15 by the process described in Example 7. M.P.×260°-262° C. (coloration occurs at 240° C.). $[\alpha]_D = -13.0°$ (c=0.972, methanol)

EXAMPLE 17

1-(4-Toluenesulfonyl)-4-hydroxy-D-proline

To 10 g (76.30 mmol) of 4-hydroxy-D-proline in 75 ml of water was added 17.45 g (91.6 mmol) of 4-toluenesulfonyl chloride and 17 g (160.2 mmol) of sodium carbonate and the mixture was allowed to stir for 24 hours at room temperature. The reaction was then acidified to pH 1 by the careful addition of 10% aqueous HCl solution and the product was isolated by filtration. After drying at high vaccum, 18.5 g of product was isolated (85% yield). M.P.=145°-146° C.

EXAMPLE 18

(2S, 4S)-2-Hydroxymethyl-4-hydroxy-1-(4-toluenesulfonyl) pyrrolidine 4.14 g (109.5 mmol) of sodium borohydride was suspended in 150 ml of THF at 0° C. and 17.6 ml (142.2 mmol) of borontrifluoride etherate was added dropwise over a period of 10 minutes. 15.6 g (54.7 mmol) of 1-(4-toluenesulfonyl)-4-hydroxy-D-proline was added in portions and the mixture was allowed to stir at room temperature for 16 hours. The reaction was then cooled to 0° C. and quenched with methanol; 10% aqueous HCl solution was then added and the mixture was gently heated to 60° C. for 1 hour. The pH of the reaction was adjusted to neutral with 50% aqueous sodium hydroxide solution and the volatiles were evaporated under reduced pressure. The product was then isolated via filtration and the filter cake was washed with water. Drying under vacuum at 60° C. for 12 hours yielded 10.2 g of the product as a white solid in 69% yield. M.P.=103°-105° C.

EXAMPLE 19

(2R, 4S)-2-Chloromethyl-4-chloro-1-(1-toluenesulfonyl)pyrrolidine

To 1 g (3.68 mmol) of (2S, 4S)-2-hydroxymethyl-4-hydroxy-1-(4-toluenesulfonyl)pyrrolidine in 6 ml of pyridine was added 1.76 g (9.21 mmol) of p-toluenesulfonyl chloride and the mixture was allowed to stir at room temperature for 2 hours and then heated to 95° C. for 2 additional hours. The reaction was then quenched with 10% aqueous HCl solution and extracted with methylene chloride. Chromatography of the resulting oil on silica gel (25% ethylacetate-75% hexane) provided 0.75 g of product (53% yield). M.P.=103°-105° C.

EXAMPLE 20

(1R,4R)-2-(4-Toluenesulfonyl)-5-methyl-2,5-diazabicyclo-[2.2.1]heptane

A Parr bottle was charged with 0.5 g (1.29 mmol) of (2R,4S)-2-chloromethyl-4-chloro-1-(4-toluenesulfonyl)-pyrrolidine and 6 ml of methanol and the bottle was tared. Methylamine gas was then bubbled through the methanol solution until 0.4 g (12.9 mol) of the gas had dissolved. The bottle was then sealed and heated to 110° C. After heating for 16 hours, the reaction was cooled and the solvent was evaporated at reduced pressure. The residual solids were partitioned between 50 ml of methylene chloride and 40 ml of 10% aqueous NaOH solution. The layers were separated and the organic layer was washed with 40 additional milliliters of 10% aqueous NaOH solution, and then dried over $Na_2SO_4$. Evaporation of the solvent under reduced pressure provided 309 mg of the desired product which represents a 90% yield. M.P.=82°-87° C. $[\alpha]_D = -16.8°$ (c=1.038, $CH_3OH$).

EXAMPLE 21

1-(Carbobenzyloxy)-4-hydroxy-L-proline

To 20 g (152.5 mmol) of 4-hydroxy-L-proline in 35 ml of water was added 36.7 g (436.8 mmol) of sodium bicarbonate and the mixture was cooled to 10° C. before 32.5 g (190.5 mmol) of benzylchloroformate wa added dropwise. The cooling bath was then removed and the mixture was allowed to stir for 24 hours at room temperature. The pH of the reaction was then adjusted to 1 with concentrated HCl solution and the mixture was extracted with 3×100 ml portions of methylene chloride. The organic layers were dried over $Na_2SO_4$ and evaporated in vacuum to provide 36.4 g of the product as an oil (90% yield). $NMR(CDCl_3)$: 7.30 (m,5H, aromatic), 5.12 (m,2H), 4.50 (m,2H), 4.36 (m,2H), 3.6 (m,2H), 2.38 (m,2H).

EXAMPLE 22

(2S,4R)-2-Hydroxymethyl-4-hydroxy-1(carbobenzyloxy)pyrrolidine

To 200 ml (0.2 mol) of borane. THF complex was added 27.8 g (0.1 mol) of 1-(carbobenzyloxy)-4-hydroxy-L-proline in 50 ml of THF at 0° C. After 16 hours of stirring at room temperature, 100 ml of water was added carefully followed by 12 ml of 6N aqueous HCl solution and the mixture was extracted with 3×100 ml of methylene chloride. The combined organic extracts were dried over $MgSO_4$ and evaporated to yield 22.6 g of the product (oil, 90% yield). $NMR(CDCl_3)$: 7.40 (m,5H), 5.10 (m,2H), 4.90 (m,1H), 4.65 (m,1H), 4.35 (m,1H), 4.17 (m,1H), 3.60 (m,3H), 2.05 (m,1H), 1.70 (m,1H).

EXAMPLE 23

(2S,4R)-1-(Carbobenzyloxy)-2-(4-toluenesulfonyloxymethyl)-4-(4-toluenesulfonyloxy)-pyrrolidine To an ice-cold solution of 150 g (596.9 mmol) of (2R,4S)-2-hydroxymethyl-4-hydroxy-N-(carbobenzyloxy)-pyrrolidine in 0.5 l of pyridine was added 250 g (1.32 mol) of 4-toluenesulfonyl chloride in 3 portions to keep the temperature of the reaction below 15° C. for 1 hour and then warmed to room temperature. After 12 hours, an additional 125 g (656 mmol) of p-toluenesulfonyl chloride was added and the mixture was allowed to stir at room temperature for 16 additional hours. The mixture was then cooled with an ice bath and 3 l of 10% aqueous HCl solution was carefully added. The mixture was extracted with 2×250 ml of methylene chloride and dried over $MgSO_4$. Evaporation of the solvent provided 274 g of the product as an oil (82% yield). $NMR(CDCl_3)$: 7.70 & 7.40 (m,9H, aromatic), 5.0 (m,3H), 4.43 (dd,1H), 4.12 (m,1H), 4.02 (m,H), 3.70 (m,1H), 3.88 (m,1H), 2.42 (m,6H), 2.15 (m,2H).

EXAMPLE 24

(1S,4S)-2-(Carbobenzyloxy)-5-methyl-2,5-diazabicyclo[2.2.1]heptane

A Parr bottle was charged with 22 g (40.2 mmol) of (2S,4R)-1-(carbobenzyloxy)-2-(p-toluenesulfonyloxymethyl)-4-(4-toluenesulfonyloxy)-pyrrolidine and 100 ml of methanol and the bottle was then tared. Methylamine gas was bubbled through the methanol solution until 12.4 g (402 mmol) of the gas had dissolved. The bottle was then sealed and heated to 80° C. After heating for 16 hours, the reaction was cooled and the solvent was evaporated at reduced pressure. The residual solids were then partitioned between 200 ml of methylene chloride and 150 ml of 10% aqueous NaOH solution. The layers were separated and the organic layer was washed with 100 additional ml of 10% aqueous NaOH solution, and then dried over $Na_2SO_4$. Evaporation of the solvent under reduced pressure provided 9.0 g of the desired product (oil) which represents a 91% yield. $NMR(CDCl_3)$: 7.32 (aromatic, 5H), 5.1 (d,2H), 4.4 (d,1H), 3.58 (dd, 1H), 3.4 (d,1H), 3.22 (m,1H), 2.88 (m,1H), 2.7 (d,1H), 2.52 (d,1H), 2.40 (s,3H), 1.86 (d,1H), 1.7 (m,1H).

EXAMPLE 25

(1S,4S)-2-Methyl-2,5-diazabicyclo-[2.2.1]heptane 3.0 g (12.19 mmol) of (1S,4S)-2-(carbobenzyloxy)-5-methyl-2,5-diazabicyclo-[2.2.1]heptane was dissolved in 30 ml of methanol, 600 mg (0.2% by weight) of 10% Pd on carbon was added and the mixture was hydrogenated at 50 p.s.i. for 16 hours. The mixture was filtered and the solvent was evaporated and replaced by 30 ml of methylene chloride. This mixture was then dried over $K_2CO_3$ and evaporated to yield 1.25 g of the diamine product in 92% yield. $NMR(CDCl_3)$: 4.5 (broad,1H), 3.43 (broad,1H), 3.12 (broad,1H), 3.05 (d,1H), 2.68 (m,2H), 2.32 (d,1H), 2.21 (s,3H), 1.65 (d,1H), 1.44 (d,1H). $CMR(CDCl_3)$: 62.33, 57.30, 47.18, 40.70, 35.98, 35.35.

We claim:

1. A process for preparing a compound of the formula

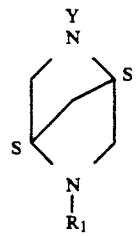

IA or the enantiomer, racemate, or acid addition salt thereof, wherein Y is hydrogen or $XR_2$, $R_1$ is hydrogen or $C_1$-$C_6$ alkyl, and X and $R_2$ are as defined below, which comprises (a) reacting a compound of the formula

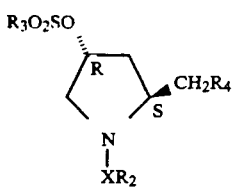

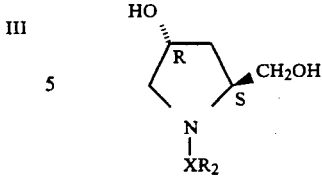

or the enantiomer or the racemate thereof, wherein X is $SO_2$ or $CO_2$, $R_2$ and $R_3$ are each independently $C_1$-$C_6$ alkyl, trifluoromethyl, benzyl, or phenyl optionally substituted by one or two $C_1$-$C_6$ alkyl, halogen, nitro, methoxy or trifluoromethyl, and $R_4$ is halogen or $OSO_2R_3$ wherein $R_3$ is as defined above, with a ($C_1$-$C_6$)alkylamine or ammonia to form a compound of the formula IA wherein Y is $XR_2$, and X, $R_1$ and $R_2$ are as defined above, and, if desired, (b) reducing or hydrolyzing the compound of formula IA wherein Y is $XR_2$ to form a compound of formula IA wherein Y is hydrogen.

2. A process according to claim 1 wherein said $C_1$-$C_6$ alkylamine is methylamine, X is $SO_2$, and $R_2$ is p-tolyl.

3. A compound of the formula

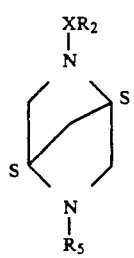

or the enantiomer or racemate thereof, wherein X is $SO_2$ or $CO_2$, $R_2$ is $C_1$-$C_6$ alkyl, trifluoromethyl, benzyl, or phenyl optionally substituted by one or two $C_1$-$C_6$ alkyl, halogen, nitro, methoxy or trifluoromethyl, and $R_5$ is $C_1$-$C_6$ alkyl.

4. A compound according to claim 3 wherein X is $SO_2$ and $R_2$ is paratolyl.

5. A compound according to claim 3 wherein X is $SO_2$, $R_2$ is paratolyl, and $R_5$ is methyl.

6. A process according to claim 1 wherein said compound of formula III is prepared by reacting a compound of the formula or the enantiomer or racemate thereof, wherein X is $SO_2$ or $CO_2$, and $R_2$ is $C_1$-$C_6$ alkyl, trifluoromethyl, benzyl, or phenyl optionally substituted by $C_1$-$C_6$ alkyl, halogen, nitro, methoxy, or trifluoromethyl, with a compound of the formula $$R_3SO_2X^1 \quad V$$

wherein $R_3$ is $C_1$-$C_6$ alkyl, trifluoromethyl, or phenyl optionally substituted by $C_1$-$C_6$ alkyl, halogen, nitro, methoxy or trifluoromethyl, and $X^1$ is halogen or $OSO_2R_3$, wherein $R_3$ is as defined above.

7. A process according to claim 6 wherein X is $SO_2$ and $R_2$ is paratolyl.

8. A process according to claim 6 wherein said compound of formula IV is prepared by reducing a compound of the formula

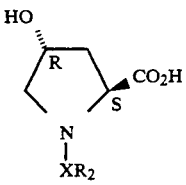

or the enantiomer or racemate thereof, wherein X is $SO_2$ or $CO_2$, and $R_2$ is $C_1$-$C_6$ alkyl, trifluoromethyl, benzyl, or phenyl optionally substituted by one or two $C_1$-$C_6$ alkyl, halogen, nitro, methoxy or trifluoromethyl.

9. A process according to claim 8 wherein said reduction is carried out with sodium borohydride in the presence of borontrifluoride etherate.

10. A process according to claim 8 wherein X is $SO_2$ and $R_2$ is paratolyl.

11. A process according to claim 8 wherein said compound of formula VI is prepared by reacting 4-hydroxy-L-proline with a compound of the formula $$R_2X\ X^1 \quad VII$$

wherein X is $SO_2$ or $CO_2$, $R_2$ is $C_1$-$C_6$ alkyl, trifluoromethyl, benzyl, or phenyl optionally substituted by one or two $C_1$-$C_6$ alkyl, halogen, nitro, methoxy or trifluoromethyl, and $X^1$ is halogen, an azide or $OSO_2R_2$, wherein $R_2$ is as defined above, in the presence of alkali metal carbonate.

12. A process according to claim 11 wherein X is $SO_2$ and $R_2$ is paratolyl.

* * * * *